United States Patent
DuPont et al.

(10) Patent No.: US 6,207,843 B1
(45) Date of Patent: Mar. 27, 2001

(54) PROCESS FOR THE PREPARATION OF N-(ALKANOYL) AMINOALKANOYLOXY BENZENESULFONATES

(75) Inventors: Jeffrey Scott DuPont, Fairfield, OH (US); Stephen Wayne Heinzman, Whitley Bay (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/319,749

(22) PCT Filed: Dec. 15, 1997

(86) PCT No.: PCT/US97/22894

§ 371 Date: Jun. 10, 1999

§ 102(e) Date: Jun. 10, 1999

(87) PCT Pub. No.: WO98/27056

PCT Pub. Date: Jun. 25, 1998

Related U.S. Application Data

(60) Provisional application No. 60/033,652, filed on Dec. 17, 1996.

(51) Int. Cl.$^7$ .................................................. C07C 231/00
(52) U.S. Cl. .................................................................. 554/69
(58) Field of Search .................................................. 554/69

(56) References Cited

U.S. PATENT DOCUMENTS

| | | | |
|---|---|---|---|
| 5,391,780 | 2/1995 | Zima et al. | 554/69 |
| 5,393,901 | 2/1995 | Zima et al. | 554/69 |
| 5,393,905 | 2/1995 | Zima et al. | 554/70 |
| 5,414,099 | 5/1995 | Heinzman et al. | 554/69 |
| 5,466,840 | * 11/1995 | Lutz et al. | 554/70 |
| 5,523,434 | 6/1996 | Burns et al. | 554/68 |
| 5,534,642 | 7/1996 | Heinzman et al. | 554/98 |

* cited by examiner

*Primary Examiner*—Deborah D. Carr
(74) *Attorney, Agent, or Firm*—C. Brant Cook; Kim William Zerby; Steven W. Miller

(57) ABSTRACT

N-(alkanoyl)aminoalkanoyloxybenzensulfonate bleach activators are prepared in an improved process using amine catalyst and/or amido solvents.

14 Claims, No Drawings

PROCESS FOR THE PREPARATION OF N-(ALKANOYL) AMINOALKANOYLOXY BENZENESULFONATES

This application is a 371 of PCT/0597/22894 filed Dec. 15, 1997.

FIELD OF THE INVENTION

The present invention relates to an improved process for synthesizing organic compounds for use as bleach activators.

BACKGROUND OF THE INVENTION

Salts of acyloxybenzenesulfonic acids are known for use as bleach activators in laundry detergents; see EPA 0 355 384 A1 and U.S. Pat. Nos. 5,534,642 and 5,414,099. As noted in the references cited hereinafter, various syntheses for such materials have been disclosed in the art. However, as can be seen from an inspection of these references, product yields are sub-optimal and the overall process can be complicated. As with any process which is conducted on a commercial scale, there is a continuing search for means to increase product yields and to otherwise facilitate plant operations. The present invention provides simple, yet effective, means for improving the process for manufacturing these bleach activator compounds.

BACKGROUND ART

U.S. Pat. No. 5,466,840 to Lutz, Zima and Bernard, issued Nov. 14, 1995; U.S. Pat. No. 5,391,780 to Zima and Williams, issued Feb. 21, 1995; U.S. Pat. No. 5,393,901 to Zima, Williams, Lutz and Dickason, issued Feb. 28, 1995; U.S. Pat. Nos. 5,393,905 to Zima. Williams and Shelton, issued Feb. 28. 1995; and 5,523,434 to Burns and Simpson, issued Jun. 4, 1996. all relate to various aspects of the synthesis and/or purification of compounds of the present type.

SUMMARY OF THE INVENTION

The present invention encompasses, in a process for preparing a sulfophenyl amido alkanoate by reacting acetoxy benzene sulfonate with an amido carboxylic acid, the improvement which comprises conducting the reaction in the presence of a tertiary amine.

The amido carboxylic acids used herein are of the formula

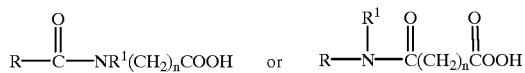

wherein R is $C_5$–$C_{21}$ hydrocarbyl, $R^1$ is selected from hydrogen and $C_1$–$C_3$ alkyl, and n is an integer from 1 to about 8. In a highly preferred mode, the amido carboxylic acid is

The tertiary amines used herein are of the formula $R^2R^3R^4N$, wherein substituents $R^2$, $R^3$ and $R^4$ may be the same or different and are members selected from the group consisting of hydrocarbyl, e.g., $C_1$–$C_{18}$ alkyl, alkenyl, branched or straight-chain, and alkoxy such as methoxy, ethoxy, propoxy, and the like, provided that any —OH substituents on the alkoxy substituents are capped with alkyl groups such as methyl. The substituents (e.g. $R^2$ and $R^3$) may be cyclized to form a ring. Preferred amines include members selected from the group consisting of tris[2-(2-methoxyethoxy)ethyl]amine, N,N-dimethyldodecylamine, and imidazole. The process uses the amine in an amount ranging from at least about 0.1, preferably from about 0.3 to about 1.0, molar equivalent based on the amido acid reactant.

The invention also encompasses in a process for preparing a sulfophenyl amido alkanoate by reacting acetoxy benzene sulfonate with an amido carboxylic acid, the improvement which comprises conducting the reaction in the presence of an (non-amido carboxylic acid) amido solvent. Again, the amido carboxylic acid is of the formula shown above and is preferably

In this process, the preferred amido solvent has a boiling point of at least about 200° C. Most preferably, the amido solvent is free from N-H substituents. Such amido solvents include members selected from the group consisting of cyclic amides, N-substituted imides and urea derivatives. Examples of amido solvents useful herein include members selected from the group consisting of 1-cyclohexyl-2-pyrrolidinone, N-methylpyrrolidone, N-acetylmorpholine, and mixtures thereof.

In another aspect, the manufacturer may elect to use the amido solvent in combination with the amine catalyst.

All percentages, ratios and proportions disclosed herein are on a mole basis, unless otherwise specified. All documents cited are, in relevant part, incorporated herein by reference.

DETAILED DESCRIPTION OF THE INVENTION

As noted above, the use of the organic compounds which can be manufactured by the improved process disclosed herein as bleach activators is known and forms no part of the present invention. Rather, the invention herein relates to an improvement in the process for manufacturing said compounds.

The invention herein comprises two aspects, and, optionally, combinations thereof In one aspect, key steps of the process are conducted in the presence of amine compounds, preferably tertiary amines, which substantially improve the yield of the desired end product. These amines seem to act as a "catalyst", inasmuch as they substantially increase product yields. However, they are typically used in higher proportions than one might expect for conventional "catalysts". Thus, it may be speculated that these amines actually function to modify the phase behavior of the reactants used in the process, thereby providing improved solubility/reactivity of the reactants. Or, it may be speculated that the amines function as a transacylation catalyst (e.g., imidazole). Whatever the reason for the improvement in the overall process, these amines may conveniently referred to as "phase transfer catalysts".

In another aspect, amido solvents are used in the reaction. These solvents provide reactant and product mixtures which are easier to work with on an industrial scale (i.e., improved processability) than the sulfur-containing solvents described in the above-cited references.

In another optional mode, combinations of the amido solvent and the amine "phase transfer catalyst" are used to improve the process, either with respect to overall product yields, overall processability, or both.

The details of a process for manufacturing preferred bleach activators such as the 4-[N-(alkanoyl)aminoalkanoyloxy]benzenesulfonate are described in U.S. Pat. No. 5,466,840 and the other patents cited above, all of which are incorporated herein by reference. Such patents can be readily referred to for experimental procedures such as reaction times, temperatures, handling techniques, purification steps, and the like.

As an overall proposition, the synthesis disclosed in this art, and which is the subject of the improved process herein, comprises the following reactions, which may be conducted in a single vessel without isolation of the ABS compound. In this regard, the reaction can comprise the joint admixture of the SPS, acetic anhydride and amido acid.

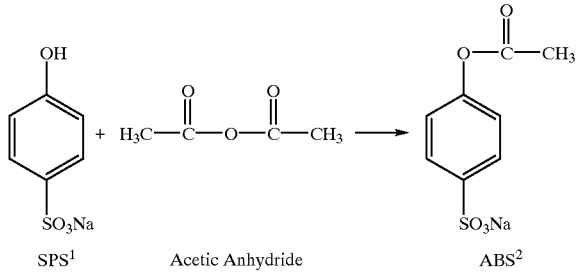

SPS[1]       Acetic Anhydride       ABS[2]

[1]Sodium salt of p-phenol sulfonate
[2]Acetoxy benzene sulfonate

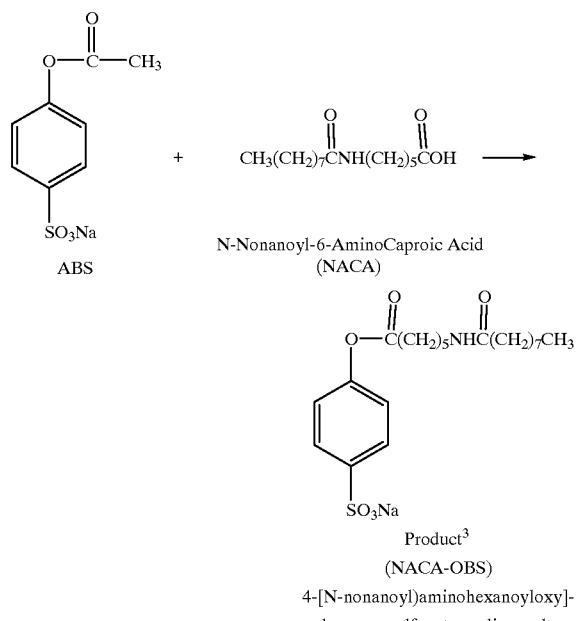

Product[3]
(NACA-OBS)
4-[N-nonanoyl)aminohexanoyloxy]-
benzene sulfonate, sodium salt

[3]Bleach activator Product

Thus the present invention comprises, in a process for preparing an N-(alkanoyl)aminoalkanoyloxy benzenesulfonate Product by reacting ABS with an amido carboxylic acid, the improvement which comprises conducting the reaction in the presence of a tertiary amine, or in the presence of an amido solvent, or both.

The following Examples illustrate the invention in more detail, but are not intended to be limiting thereof.

EXAMPLE I

The process described in Example 1 of U.S. Pat. No. 5,466,840 is repeated using the following reactants. (Example 1 of '840 is also repeated as a Control to compare Product yields.)

| Reactant | Grams | Moles |
| --- | --- | --- |
| Nonanamidohexanoic Acid | 10 | 0.0357 |
| SPS (Aldrich, 98%) | 7.8 | 0.0389 |
| Sodium Acetate (Aldrich, anhyd.) | 0.19 | 0.0023 |
| Acetic Anhydride (Aldrich) | 4.37 | 0.0428 |
| Sulfolane* Solvent (Aldrich) | 37.2 | 0.31 |
| Tris-(3,6-Dioxaheptyl Amine)** | 11.55 | 0.357 |

*Sulfolane is

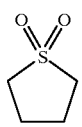

and is also referred to as tetrahydrothiophene-1,1-dioxide.
**"TDA"; Amine phase transfer catalyst of the formula tris [2-(2-methoxyethoxy)ethyl]amine. Aldrich, 95%.

The TDA is added with the addition of the sodium phenol sulfonate after all the acetic anhydride is in the reaction vessel and before vacuum. After a three hour reaction time, the resulting 4-[N-(nonanoyl)aminohexanoyloxy]benzene sulfonate (NACA-OBS) bleach activator Product is secured in high yield (above 80%, measured by $C^{13}H^1$ nmr; 95%, measured by HPLC). By contrast, the Control reaction conducted in the absence of the TDA results in a yield of about 45% (nmr)/52% (HPLC).

EXAMPLE II

The processes described in Examples 2 and 3 of U.S. Pat. No. 5,466,840 are repeated but with the addition of from about 0.1 to about 1.0 mole equivalents of the TDA. Again, product yields are substantially improved.

EXAMPLE III

The process of Example I herein is repeated using 2.3 g (0.17 mole; 0.3 equivalents based on C9 amido acid) of N,N-dimethyldodecylamine in place of the TDA. The yield of Product is 92% by HPLC analysis.

EXAMPLE IV

The process is again repeated, but using 1.2 g. (0.017 mole; 0.3 equiv. based on C9 amido acid) of imidazole in place of TDA. The reaction system is very foamy. Product yields are 95% HPLC.

EXAMPLE V

This example illustrates the process of Example I, herein, but with the replacement of the sulfolane solvent with 37 grams of 4-acetylmorpholine (Aldrich). This reaction system results in a clear, light yellow solution which is easy to handle. Product yields are above the Control, and are in the range of about 75%.

EXAMPLE VI

The process of Example V is repeated using 1-cyclohexyl-2-pyrrolidinone and N-methylpyrrolidinone, respectively, as the solvent. Yields are in the 80% range.

EXAMPLE VII

The process of Example I is repeated using 4-acetylmorpholine solvent and 0.3 equivalents of TDA. Excellent yields of product are secured.

As can be seen from the foregoing, the present process comprises an improvement over the art-disclosed processes. It will be appreciated by those skilled in the art of chemical synthesis that the applicability of the improved process herein goes beyond the reactants used in the foregoing illustrative Examples. Thus, the following materials can be employed herein.

Amido acids used herein can be of the general formula

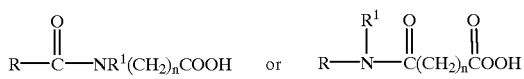

wherein R is $C_5-C_{21}$ hydrocarbyl, especially alkyl or alkenyl, and is preferably $C_6-C_{12}$ alkyl; $R^1$ can be hydrogen (preferred) or $C_1-C_3$ alkyl; n can be an integer from about 1 to about 8, preferably about 4 to about 6.

Non-sulfur solvents herein are amido materials as described above. Preferably, these solvents are any which have a boiling point of at least about 200° C. Most preferably, the ABS and amino acid are soluble in such solvents to, at least, a 1% level, preferably at least 5% to 15% (wt.). It is not necessary that the Product be soluble in the solvent.

The amount of amido solvent used can vary with the needs of the formulator. As with any solvent, a quantity sufficient to provide a tractable reaction system is employed. Typically, this will be on the order of about 1 to 200-fold the amount (wt.) of reactants being used.

In a highly preferred mode, the present invention provides an improvement in a process for preparing a 4-[N-(alkanoyl)aminoalkanoyloxy]benzenesulfonate Product by the reaction comprising:

(A) reacting an alkali metal salt of 4-hydroxybenzenesulfonic acid with a $C_2$ to $C_4$ carboxylic anhydride at a sufficient temperature (typically about 100° C.–200° C.) and time (typically about 0.5–5 hours) in a solvent to form an alkali metal salt of 4-acyloxybenzenesulfonic acid and a $C_2$ to $C_4$ carboxylic acid, wherein the alkali metal salt of 4-hydroxybenzenesulfonic acid and $C_2$ to $C_4$ carboxylic anhydride are present in a mole ratio of 1:1 to 1:40, respectively, and the solvent is present in a weight ratio of 2:1 to 50:1 based on the weight of the alkali metal salt of 4-hydroxybenzenesulfonic acid, provided that excess carboxylic anhydride is removed under reduced pressure from the reaction vessel;

(B) adding an N-(alkanoyl)aminoalkanoic acid and at least one transesterification (e.g. TDA) catalyst to the reaction product of Step (A) and heating at a temperature of about 150° C. to about 250° C. for about 0.5 to 10 hours and pressure sufficient to maintain reflux of the solvent and to remove the $C_2$ to $C_4$ carboxylic acid from the reaction vessel, to form a reaction mixture containing an alkali metal salt of 4-[N-(alkanoyl)aminoalkanoyl-oxy] benzenesulfonate, wherein the moles of the N-(alkanoyl) aminoalkanoic acid added is 0.7 to 5 times the moles of the alkali metal salt of 4-hydroxybenzenesulfonic acid used in Step (A);

wherein said improvement comprises conducting said reaction in the presence of from about 0.01 to about 1 equivalents of a tertiary amine.

In another mode, the aforesaid improvement comprises conducting said reaction (with or without the amine catalyst) in an amide solvent as described herein. In either instance, the desired reaction Product can be recovered using steps (C), (D), (E) of U.S. Pat. No. 5.466,840, or by any other recovery sequence.

What is claimed is:

1. In a process for preparing an N-(alkanoyl) aminoalkanoyloxy benzenesulfonate by reacting acetoxy benzene sulfonate with an amido carboxylic acid, the improvement which comprises conducting the reaction in the presence of at least about 0.1 mole equivalent based on the amido carboxylic acid of a tertiary amine selected from the group consisting of tris[2-(2-methoxyethoxy)ethyl) amine, N,N-dimethyldodecylamine, imidazole and mixtures thereof.

2. A process according to claim 1 wherein the amido carboxylic acid is of the formula

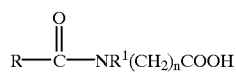

wherein R is $C_5-C_{21}$ hydrocarbyl, $R^1$ is selected from hydrogen and $C_1-C_3$ alkyl, and n is an integer from 1 to about 8.

3. A process according to claim 2 wherein the amido carboxylic acid is

4. A process according to claim 1 wherein the tertiary amine is a member selected from the group consisting of tris[2-(2-methoxyethoxy)ethyl]amine, N,N-dimethyldodecylamine, and imidazole.

5. A process according to claim 1 wherein the amine is used in an amount from about 0.1 to about 1.0 mole equivalents based on the amido carboxylic acid of the tertiary amine.

6. In a process for preparing an N-(alkanoyl) aminoalkanoyloxy benzenesulfonate by reacting acetoxy benzene sulfonate with an amido carboxylic acid, the improvement which comprises conducting the reaction in the presence of an amido solvent selected from the group consisting of cyclic amides, N-substituted imides, urea derivatives and mixtures thereof.

7. A process according to claim 6 wherein the amido carboxylic acid is of the formula

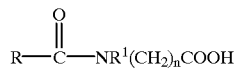

wherein R is $C_5-C_{21}$ hydrocarbyl, $R^1$ is selected from hydrogen and $C_1-C_3$ alkyl, and n is an integer from 1 to about 8.

8. A process according to claim 7 wherein the amido carboxylic acid is

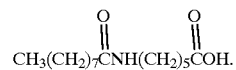

9. A process according to claim 6 wherein the amido solvent has a boiling point of at least about 200° C.

10. A process according to claim 9 wherein the amido solvent is free from N-H substituents.

11. A process according to claim 6 wherein the amido solvent is a member selected from the group consisting of cyclic amides, N-substituted imides and urea derivatives.

12. A process according to claim 6 wherein the amido solvent is selected from the group consisting of 1-cyclohexyl-2-pyrrolidinone, N-methylpyrrolidone, N-acetylmorpholine, and mixtures thereof.

13. A process according to claim 1 which is conducted in the presence of an amido solvent.

14. A process according to claim 6 which is conducted in the presence of a tertiary amine.

* * * * *

UNITED STATES PATENT AND TRADEMARK OFFICE
CERTIFICATE OF CORRECTION

PATENT NO. : 6,207,843 B1  
DATED : March 27, 2001  
INVENTOR(S) : Jeffrey S. Dupont et al.

Page 1 of 1

It is certified that error appears in the above-identified patent and that said Letters Patent is hereby corrected as shown below:

<u>Title page,</u>  
FOREIGN PATENT DOCUMENTS: add  
-- EP 355,384      07/15/89  
    WO 92/16492      01/10/92 --

Signed and Sealed this

Eighteenth Day of December, 2001

Attest:

JAMES E. ROGAN  
*Attesting Officer*     *Director of the United States Patent and Trademark Office*